United States Patent [19]

Selenke

[11] Patent Number: 4,958,622

[45] Date of Patent: Sep. 25, 1990

[54] HYPODERMIC SYRINGE FOR TAKING AND TRANSPORTING A SPECIMEN

[76] Inventor: William M. Selenke, 18 Gambier Cir., Cincinnati, Ohio 45218

[21] Appl. No.: 493,435

[22] Filed: May 11, 1983

[51] Int. Cl.$^5$ ............................................. A61B 5/14
[52] U.S. Cl. ................................... 128/765; 604/192; 604/220
[58] Field of Search ........................... 128/760–765; 604/27, 209–210, 220, 224, 183, 192, 197, 208, 263

[56] References Cited

U.S. PATENT DOCUMENTS

| | | | |
|---|---|---|---|
| 554,614 | 2/1896 | Beyer | 604/236 |
| 1,456,469 | 5/1923 | Schwidetzky | 604/183 |
| 2,541,621 | 2/1951 | Thompson | 604/92 |
| 2,594,621 | 4/1952 | Derrick | 128/764 |
| 2,739,591 | 3/1956 | Yochem | 604/210 |
| 3,370,588 | 2/1968 | Burke | 604/192 |
| 3,492,993 | 2/1970 | Tillmann | 604/208 |
| 3,696,806 | 10/1972 | Sausse | 128/764 X |
| 3,827,601 | 8/1974 | Magrath et al. | 222/83 |
| 3,865,236 | 2/1975 | Rycroft | 604/263 X |
| 3,933,439 | 1/1976 | McDonald | 128/765 X |
| 3,952,729 | 4/1976 | Libman et al. | 128/762 |
| 3,978,846 | 9/1976 | Bailey | 128/762 |
| 4,011,685 | 3/1977 | Boyd et al. | 47/57.5 |
| 4,051,852 | 10/1977 | Villari | 604/183 |
| 4,200,478 | 3/1980 | Jacino et al. | 156/94 |
| 4,212,309 | 7/1980 | Moorehead | 128/765 X |
| 4,316,473 | 2/1982 | Beskin | 128/763 |
| 4,370,987 | 2/1983 | Bazell et al. | 128/760 |

FOREIGN PATENT DOCUMENTS 0855947 5/1940 France .................. 604/183

Primary Examiner—Angela D. Sykes
Attorney, Agent, or Firm—Wood, Herron & Evans

[57] ABSTRACT

A hypodermic syringe is disclosed which facilitates both the transportation of a fluid specimen therein and the ready accessibility of the specimen in the syringe. The hypodermic syringe is provided with a port in the syringe barrel proximate the needle neck of the barrel. Location of the port in this area facilitates the introduction of sampling instruments into the interior chamber of the syringe. A fluid-tight cap is provided for the port. A boss is also provided spaced inwardly along the exterior of the barrel of the syringe near the plunger opening of the syringe, to thereby incline the syringe to promote pooling of specimen fluids in the area of the port. A rigid protective cover for a hypodermic needle mounted on the needle neck of the syringe is removably received on the barrel of the syringe, and is spaced radially from the neck, and surrounds the hypodermic needle to protect the needle during transport.

A series of spaced detents extend longitudinally along the elongated body portion of the syringe plunger. A resilient member carried on the barrel of the syringe adjacent the plunger opening is biased to engage the detents of the body portion of the plunger, whereby the resilient member permits withdrawing movement of the plunger and prevents reinserting movement, such as might be caused by accident during transport of a specimen containing syringe.

31 Claims, 1 Drawing Sheet

HYPODERMIC SYRINGE FOR TAKING AND TRANSPORTING A SPECIMEN

Field of the Invention

This invention relates generally to hypodermic syringes, and is particularly related to a hypodermic syringe which can be used to obtain a fluid specimen, serve as a safe transport container for the specimen, and facilitate removal of a specimen from within the syringe.

Background of the Invention

Hypodermic syringes are well known, and are routinely used to obtain fluid or liquid specimens for diagnostic testing. For example, body fluids so collected include absess fluids, peritoneal fluids, bone joint fluids and so forth. Likewise, certain types of urine samples such as superpubic aspirates and urine samples from indwelling Foley catheters are collected by means of hypodermic syringes. The specimen must be first obtained from the patient through the insertion of the hypodermic needle of the syringe into the fluid containing area, with the fluid specimen then drawn into the interior chamber of the syringe through withdrawing action of the syringe plunger. Next, the specimen obtained must be somehow transported to the examining laboratory for analysis. Lastly, the specimen must be removed from its transport container for testing.

Specimens collected through the use of a hypodermic syringe are oftentimes expressed into a second container for transport to the laboratory for testing. In some instances, the fluid specimens are transported in the syringe itself. The transportation of specimens in the syringe is advantageous for several reasons. First, and most obvious, the sample does not need to be expressed into a second container. This transferring process of course requires extra time for the physician, as well as the expense of a second container. Secondly, when fluids from closed or air-isolated spaces are transported to the laboratory in the syringe, such fluids are obviously maintained in a closed or substantially closed environment. This is important particularly where it is necessary to prevent any anaerobic bacteria from being exposed to atmospheric oxygen. Expressing the fluid into a second container increases the risk that the specimen will be exposed to contaminating atmosphere.

Hypodermic syringes which are presently used for obtaining such routine fluid specimens are not suitably adapted for the relatively rough handling which they are subjected to during transportation. For instance, the close conforming tubular sheath which is typically used to protect the needle during transport is usually only loosely attached about the needle, and can be easily flexed. Since the base of the needle itself is typically only loosely attached to the neck of the barrel of syringe in a friction fit, such flexing can cause the needle to become loosened, with the result that fluid may leak or be exposed to contamination. Furthermore, once the plunger has been partially withdrawn from the barrel in obtaining the specimen, there is no means for preventing the plunger from being reinserted. Handling or jostling during transport can thereby express some of the specimen and expose handlers to potentially hazardous matter.

Another difficulty in using the ordinary hypodermic syringe as a transport container for the specimen presents itself once the specimen has arrived at the laboratory. Ordinarily, the fluid will have to be expressed for purposes of examination. In some instances, the fluid may have clotted and thus will obstruct its exit from the syringe. In other instances, excessive fluid may be expressed out, particularly in larger diameter syringes, due to control problems inherent in manually expressing small volumes of fluid.

Particular problems are presented by urines which are transported to the laboratory in the syringes in which they were collected. Standard laboratory procedures require that a calibrated or dairy loop be placed into the urine so that a specific volume will adhere to the loop. Thus, a loop with an overall diameter of about 5 mm will typically be placed directly into a volume of the urine. When the urine arrives at a laboratory in a syringe, it must be either expressed into a second container, or the plunger must be removed to allow access to the volume of urine contained within the syringe barrel. When the plunger is removed, however, urine can leak out of the needle, creating an unpleasant and hazardous condition for the handler.

Summary of the Invention

In light of these shortcomings of using conventional hypodermic syringes for transport of the specimens obtained with the syringe, and the difficulties in removing certain specimens from the syringe once it is at the examining laboratory, it is the general object of this invention to provide an improved syringe for the safe transport of specimens in the syringe in which the specimen was originally obtained, and which facilitates the access to and/or removal of the specimen from the syringe when desired.

It is a more specific object of this invention to provide a port in the side of the barrel of a hypodermic syringe which is proximate the neck or narrowed portion upon which the hypodermic needle is received, the port communicating with the interior of the chamber, and through which port sampling instruments can be introduced with little difficulty directly into the interior of the chamber, and further providing a fluid-tight closure for the port.

It is another object of the invention to provide a protective cover surrounding the hypodermic needle which is firmly secured to the barrel of the syringe to thereby prevent any flexing or loosening of the needle during transport. Commensurate with this object is to provide this cover in a manner which will insure a fluid-tight fit of the cover on the barrel to thereby prevent the escape of any specimen leaking from the syringe in the event that the needle is dislodged during transport.

Yet another object of the invention is to provide a mechanism for preventing the inadvertent or accidental reinsertion of a syringe plunger within the barrel to thereby prevent inadvertent or accidental expression of fluid specimen.

These and other objects are accomplished by this invention which includes a hypodermic syringe having an enlarged port in the side of the syringe barrel proximate the narrowed opening of the syringe communicating with the hypodermic needle. The port communicates with the interior of the chamber, and is of a sufficient width such that sampling instruments, such as a 5 mm loop, can be easily introduced into the interior of the chamber and into specimen fluid contained therein.

Syringes with side ports have of course been known in the prior art, such as U.S. Pat. No. 1,456,469 and U.S.

Pat. No. 2,541,621. These patents, however, are merely illustrative and it is not intended to suggest that they are the only or most pertinent background patents. Such patents do not disclose in a syringe an enlarged port which is located proximate the narrowed needle opening for accessing the interior chamber of the syringe with sampling instruments to thereby withdraw fluid samples from the syringe.

The port is further provided with a fluid-tight closure or cap, which may be of a screw on or snap on fit. The improved syringe further includes an elongated boss spaced inwardly along the exterior of the barrel near the plunger opening of the syringe which serves to incline the syringe on a flat surface to promote pooling of specimen fluids in the area of the port.

In a preferred embodiment of the invention, the barrel of the syringe is provided with an annular shaped extension or collar which surrounds and is radially spaced from the neck of the syringe which receives the hypodermic needle. A rigid elongated cover is detachably received on the collar in a fluid-tight fit, the cover having an interior recess sufficiently long to receive the needle therein without the needle contacting the cover interior. Being rigidly attached to the barrel of the syringe and spaced from the needle, the cover serves to adequately protect the hypodermic needle during transport, as well as contain any fluid which might escape should the needle become dislodged or should fluid otherwise leak from or be accidentally expressed from the syringe.

A preferred form of the invention also provides for a mechanism for preventing the plunger of the syringe from being accidentally or inadvertently reinserted into the barrel, such as during transport of the specimen containing syringe. This mechanism comprises a series of spaced detents or notches extending longitudinally along the elongated body portion of the plunger. For example, where the plunger has an elongated body portion which has a pair of opposed longitudinally extending ribs, each of such ribs has a regular series of notches spaced along a portion of its length. One-way movement of the plunger permitting withdrawal of the plunger from the chamber and preventing reinsertion movement of the plunger within the chamber is accomplished by a resilient member carried on the exterior of the syringe barrel and adjacent to the plunger opening.

The resilient member has a portion which, in one embodiment, is in the form of a finger which is angled radially inwardly relative to the axis of the barrel and extending in the direction of withdrawal of the plunger from the barrel. The tip of the resilient member is biased to engage the detents of the body portion of the plunger seriatim as the plunger is withdrawn from the chamber, by alternatingly riding along the body portion of the plunger and then dropping into and engaging a detent. Due to the bias and angularity of the resilient member, the plunger can only be withdrawn from the barrel and cannot be pushed back in. In its preferred form, the resilient member is carried on a flexible clip which is removably attached to the barrel, such that the clip can be simply removed to depress or reinsert the plunger, if desired.

The foregoing objectives, features and advantages of the present invention will be more readily understood upon consideration of the following detailed description of the invention taken in conjunction with the accompanying drawings, in which:

Detailed Description of the Invention

The improved hypodermic syringe of this invention is designed to be used to gather a fluid specimen, to safely transport the specimen to the laboratory for testing, and to facilitate the removal of the specimen from the syringe once at the testing facility. The improved syringe advantageously reduces the cost of obtaining and analyzing the specimen through the elimination of the need for an intermediate transport container, as well as improving the efficiency of those personnel who must obtain the specimens and those who must thereafter examine the specimens.

Figure 1:
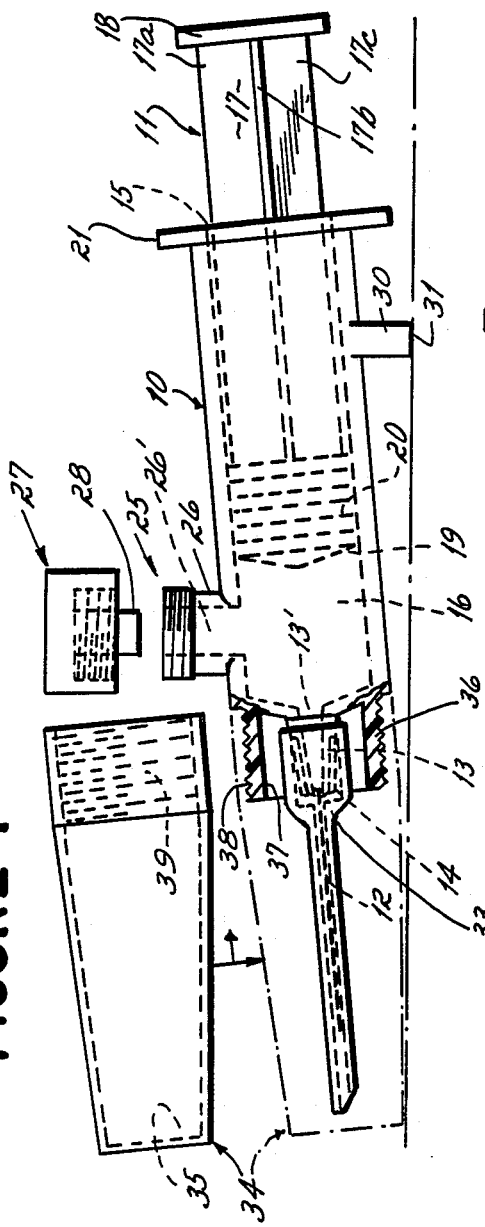
FIG. 1 is an elevational view of the improved syringe of this invention with the protective needle cover and port cap disassembled for clarity.

Referring now more particularly to FIG. 1, the improved hypodermic syringe comprises a conventional hypodermic syringe having a hollow cylindrical barrel 10 and a plunger piston 11. A hollow hypodermic needle 12 is received on a neck 13 of the barrel surrounding a narrowed opening 13'. The end of the barrel 10 opposite from the narrowed opening 13' has an enlarged opening 15 into which the plunger 11 is slidably received. The hypodermic needle 12 is provided with a collar or bowl 14 around the base, which bowl is received on the neck 13, such as by a simple friction fit thereon. The neck 13 has a passage through which fluid from the barrel interior 16 can flow on its way to the needle, such as when the plunger 11 is inserted in the barrel and moved in the direction of the narrowed opening 13'.

The plunger 11, being conventional in form, has an elongated body portion 17, which herein consists of a beam having an X-shaped cross section presenting four joined ribs 17a, 17b, 17c and 17d which are normal to each other. The rearward end of the plunger 17 has a portion 18 which facilitates pushing and pulling of the plunger within the barrel 10. The forward end of the plunger 17 carries a plunger head 19 which includes resilient gasket portion 20. Gasket portion 20 engages the interior side walls of the barrel 10 to thereby provide a fluid tight fit of the plunger head within the barrel.

Surrounding the plunger opening is a flange 21 which extends radially from the exterior of the barrel around at least a portion of the circumference of the barrel. The flange provides a leverage surface for use of the plunger 17.

The barrel 10 and the plunger 11 may be of any suitable material, such as glass or plastic, and the exterior thereof may be provided with gradations to indicate the quantity of fluid within the interior chamber. The hollow hypodermic needle 12 will typically be formed of metal. The hypodermic syringe as heretofore described is of course well known in the art.

Where a hypodermic syringe is used to obtain a fluid specimen, such as abess fluids or urine specimens, the needle 12 will be inserted into a fluid containing area, and the plunger withdrawn from the barrel an appropriate distance to thereby cause a desired amount of fluid to be drawn through the hollow needle and into the interior chamber 16. To facilitate access to a fluid specimen so drawn, such as when the specimen has been transported to the testing laboratory, a port generally designated at 25 is provided in the side wall of the barrel 10.

The port 25 is of an enlarged diameter to permit ready access to the interior of the chamber 16 for the introduction of sampling instruments directly into the fluid contained therein. For example, in the testing of urine specimens, a 5 mm loop is typically employed which must be inserted directly into a volume of the urine to be tested. Provision of a port 25 in the side of the barrel 10 which is wide enough to permit the loop to pass therethrough and into the chamber 16 thus advantageously permits such sampling without the need to either express urine into another container or remove the plunger 17 completely from the barrel 10 to thereby access the chamber 16 through the plunger opening 15.

The port 25 has a tubular extension 26 of small vertical height which extends generally radially from the barrel 10. The extension 26 is canted at a slight angle for reasons which will be explained hereafter. Location of the port proximate the narrowed opening of the neck 13 is deemed to be of significance, particularly for access to small quantities of specimen fluids which might not otherwise be obtainable, and further for pooling of fluids at this end of the barrel.

The port is provided with a fluid-tight closure 27, which in this illustrated embodiment takes the form of a cap which is threadably received on the tubular extension 26. A snap-on or other type cap might of course be utilized with the same effect. The cap 27 herein is additionally provided with an interior protuberance 28 which projects downwardly from the underside of the cap and which is sized to be slidably received in the shaft 26' formed by the tubular extension 26 and tightly embraced therein to further ensure a fluid-tight fit.

A boss 30 is located on the exterior of the barrel 10 on the side of the barrel opposite of the port 25. The boss is elongated and extends generally tangentially to the side of the barrel, and has a flattened lower portion 31. The boss 30 is spaced inwardly from the flange 21 a sufficient distance to permit easy manipulation of the syringe in obtaining or expressing fluid without interference from the boss 30. The boss 30 has a small vertical height so that, when the syringe is placed on a level surface on the flattened lower portion 31, the small vertical height of the boss serves to raise the rearward portion of the syringe barrel 10 inclining the syringe. This serves to pool liquid specimen in the forward portion of the chamber 16 and in the vicinity of the port 25.

Since the barrel 10 will be inclined with respect to the horizontal due to the presence of the boss 30, the tubular extension 26 of the port 25 is consequently canted with respect to the barrel side, such that the shaft 26' of the port is substantially vertical with respect to the horizontal surface upon which the syringe rests.

The hypodermic syringe will ordinarily be provided with a protective sheath 33 for the needle 12. The sheath, typically made of a rigid plastic, is formed to closely surround the needle 12 and slide over the bowl 14 of the needle in a friction fit. Since the sheath 33 so closely surrounds the needle 12, deflection of the sheath, such as might occur during transport or rough handling, in turn causes deflection of the bowl 14 of the needle. This can loosen the bowl 14 on the neck 13 of the syringe, and cause the bowl 14 to become separated from the neck 13. Fluid contained within the syringe can consequently leak out, contaminating both the specimen being transported as well as the handlers of the syringe. A protective cap 34 is therefore provided to prevent any deflection of the needle and sheath 33, to protect the needle during transport and provide the additional safety feature of a fluid tight cap surrounding the needle. The rigid plastic cover 34 is generally conical in shape in this embodiment, and is provided with an interior space 35 sufficiently long to easily surround the needle 12 and sheath 33.

A collar 36, which herein is an annular extension of the forward portion of the syringe barrel 10, receives the protective cover 34. The interior wall 37 of the collar is radially spaced from the neck 13, bowl 14 and base of the sheath 33 to prevent any contact between the protective cover 34 and the needle and sheath which might cause the needle to become dislodged from the neck 13. The collar 36 is provided with screw threads 38 on at least a portion of its exterior for receiving matched screw threads 39 of the protective cover 34 in a fluid-tight engagement. This fluid-tight seal surrounding the needle provides an extra measure of protection in the event that the needle does become dislodged and leakage from the syringe occurs.

It will of course be recognized that although a screw engagement of the protective cover 34 is described herein, a snap-on cover could be used with equal effectiveness. Further, although a collar 36 which is an extension of the syringe barrel is shown herein, the protective cover 34 could be adapted to attach directly to the syringe barrel 10. The use of the collar 36 is considered to be particularly advantageous, however, due to the need to place the port 25 in as close proximity to the neck 13 of the syringe as possible.

Figure 2:
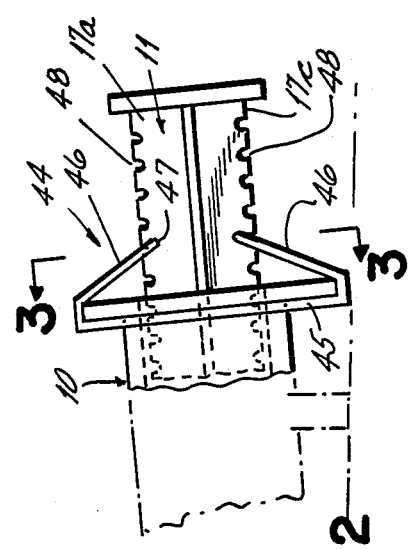
FIG. 2 is a partial elevational view of a hypodermic syringe including the one-way plunger mechanism.
Figure 3:
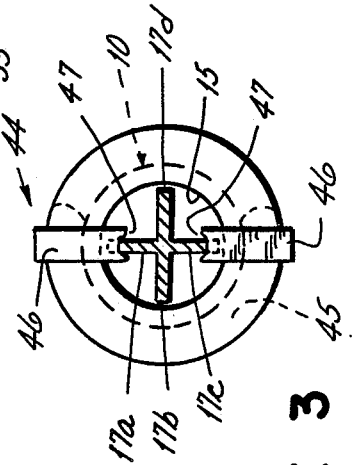
FIG. 3 is a cross-sectional view taken along the line 3—3 of FIG. 2.

In obtaining a specimen with the syringe, the plunger 11 will be partially withdrawn within the barrel 10 to thereby draw fluid material into the chamber 16. The plunger 11 will obviously have to remain in this partially withdrawn configuration during transport of the syringe to the testing laboratory. In order to prevent the plunger 11 from being accidentally or inadvertently reinserted within the barrel 10 and thereby causing undesired expression of specimen from the syringe, a one-way plunger mechanism is provided for the syringe, and is depicted in the modified embodiment shown in FIGS. 2 and 3.

With particular reference to those figures, this one-way mechanism comprises a one-way clip generally indicated at 44. As shown here, the clip 44 includes a generally C-shaped base member 45 which is adapted to conform to a portion of the circumference of the syringe barrel 10. The C-shaped base 45 snap-fits about the barrel 10, preferably being located in abutting relationship with the flange 21 of the syringe.

Extending from the base 45 of the one-way clip are opposed resilient members 46, which herein are in the form of fingers. The fingers 46 extend perpendicularly from the base 45 and then angle inwardly and toward each other. With respect to the one-way clip 44 when mounted on the syringe barrel 10, the fingers 46 extend rearwardly and then angle radially inwardly relative to the axis of the barrel 10, extending in the direction of withdrawal of the plunger from the barrel. Each of the fingers in this embodiment is provided with a notch 47, for reasons which will be made immediately apparent. The clips 44 can advantageously be made of rigid or semi-rigid plastic.

The conventional plunger 11 is modified to provide for a series of spaced detents or notches 48 along a substantial portion of at least two opposed ribs of the plunger 11, such as 17a and 17c. A notch 48 need be only of a small depth.

In use, the plunger 11 will be oriented with respect to the clip 44 so that the notched ribs 17a and 17c will be respectively received within the notches of one of the opposed fingers 46. The resilient fingers 46 are sufficiently biased so that finger notches 47 will be caused to drop into and engage the notches 48 of the respective ribs. It will thus be seen that as the plunger 11 is withdrawn from the syringe 10, the fingers 46 will alternately ride along the surface of the ribs 17a, 17c and engage rib notches 48 seriatim The angled fingers 46 thus permit only withdrawal movement of the plunger 11, and prevent the plunger from being reinserted within the barrel 10. Inadvertent or accidental reinsertion of the plunger such as might occur during transport of the syringe is thus prevented. If it is desired to reinsert the plunger, such as for expression of the specimen at the testing laboratory, the snap-on clip 44 is removed and the plunger operated.

The one-way clip 44 as previously described is of course a presently preferred embodiment of the invention. Any kind of a resilient member which is biased to engage within detents provided along the syringe plunger to provide such one-way movement is considered to be within the scope of this invention.

Thus, while the invention has been described in connection with certain presently preferred embodiments, it will be immediately obvious to those skilled in the art that many modifications to the structure, arrangement, portions, elements, materials, and components can be used in the practice of the invention without departing from the principles of this invention.

What is claimed is:

1. A hypodermic syringe for obtaining and transporting a fluid specimen comprising
   a barrel having a narrowed opening at a forward end and a plunger opening at a rearward end and an interior chamber defined within said barrel,
   a plunger sized to pass through the plunger opening into the interior chamber of said barrel,
   means for accessing the interior chamber of said barrel located at a point proximate the narrowed opening, said accessing means comprising an extension which defines a hollow shaft communicating with the interior chamber, the extension being canted at an angle relative to and extending from said barrel,
   a substantially fluid-tight closure means for said accessing means, and
   means for supporting the syringe in a skewered position with respect to horizontal located at a point proximate the rearward end of said barrel, such that when the syringe is placed on a horizontal surface with said supporting means in contact with the horizontal surface the syringe is inclined with the rearward end elevated relative to the forward end with the extension of said accessing means being substantially perpendicular to the horizontal surface.

2. The hypodermic syringe of claim 1 wherein said closure means is a cap for said extension.

3. The hypodermic syringe of claim 2 wherein the narrowed opening terminates in a neck on which is received a hypodermic needle, and further including an annular shaped extension of the barrel surrounding the neck and radially spaced therefrom, and a rigid elongated cover detachably received on the annular extension in a substantially fluid-tight fit, the cover having an interior recess sufficiently long to receive the needle therein, the elongated cover serving to protect the needle.

4. The hypodermic syringe of claim 2 wherein the plunger is provided with a series of spaced detents in a line along the longitudinal axis of the plunger, and detent engaging means on the barrel, the detent engaging means including a resilient member biased to engage the detents of the plunger such that the plunger can be slidably moved away from the narrow opening but is prevented from moving toward the narrowed opening.

5. The hypodermic syringe of claim 1 wherein said supporting means is a boss spaced inwardly along the barrel from the rearward end, the boss having generally a flat bottom.

6. The hypodermic syringe of claim 1 wherein said supporting means is a flange extending from said barrel immediate adjacent the plunger opening, said flange having generally a flat bottom on a side of said barrel opposite that of said accessing means and also being adapted for manipulating said plunger.

7. A hypodermic syringe for obtaining a fluid specimen comprising
   a barrel having a forward end and a rearward end and an interior chamber defined by an interior barrel sidewall, said barrel further having a narrowed opening at the forward end extending into a neck and a plunger opening at the rearward end and a flange extending radially from said barrel adjacent the plunger opening for manipulating a plunger,
   a plunger sized to pass through the plunger opening into the interior chamber having resilient sealing means thereon for engaging the interior barrel sidewall, such that when said plunger is passed through the plunger opening said plunger is slidably received in the interior chamber of said barrel and tightly embraced therein in a fluid-tight fit,
   a hypothermic needle received on the neck of the narrowed opening,
   a port in the barrel located proximate the narrowed opening, said port comprising an extension which defines a hollow shaft communicating with the interior chamber of said barrel through which a sampling instrument can be introduced into the interior chamber, the extension being canted at an angle relative to and extending from said barrel,
   a substantially fluid-tight closure for said port, and
   a boss spaced inwardly along the barrel near the flange, said boss having a generally flat bottom, such that the syringe when placed on a horizontal surface with said boss in contact with the horizontal surface will be inclined with the plunger opening raised relative to the narrow opening promoting pooling of a specimen fluid near the narrowed opening and said port with the extension of said port being substantially perpendicular to the horizontal surface when the syringe is so placed on the horizontal surface.

8. The hypodermic syringe of claim 7 further including an annular shaped extension of said barrel surrounding the neck and radially spaced therefrom, and a rigid elongated cover detachably received on the annular extension in a substantially fluid-tight fit, said cover having an interior recess sufficiently long to receive said needle therein, the elongated cover serving to protect said needle.

9. The hypodermic syringe of claim 7 wherein said closure has a protuberance slidably received in the shaft and tightly embraced therein when said closure is placed on said port.

10. The hypodermic syringe of claim 7 wherein said plunger is provided with a series of spaced detents extending in a line along the longitudinal axis of said plunger, and detent engaging means on said barrel, said detent engaging means including a resilient member biased to engage the detents of said plunger such that said plunger can be slidably moved away from the narrowed opening but is prevented from moving toward the narrowed opening.

11. The hypodermic syringe of claim 10 wherein said detent engaging means is removably attached to said barrel adjacent the plunger opening.

12. In a hypothermic syringe for obtaining and transporting a specimen for testing, the syringe comprising
a barrel having a forward end and a rearward end and an interior chamber defined within said barrel, said barrel further having a narrowed opening at the forward end extending into a neck and a plunger opening at the rearward end,
a plunger sized to pass through the plunger opening into the interior chamber and embraced therein in a fluid-tight engagement,
a hypothermic needle received on the neck,
a side port in said barrel for accessing the interior chamber with a sampling implement, said side port being located adjacent the narrowed opening,
a removable cap engaging said side port in a fluid-tight fit,
a flange extending from said barrel adjacent the plunger opening for manipulating said plunger, and
a protective cover for the needle, said protective cover being removably received on the barrel of the syringe and spaced radially from the neck, said protective cover when in use surrounds said needle and is spaced therefrom to protect said needle during transport.

13. The improved hypothermic syringe of claim 12 wherein said side port has a tubular extension of small vertical height extending generally radially from said barrel, a portion of said tubular extension being screw threaded, said removable cap being match threaded for a screw fit with said side port, said removable cap further including a protuberance which is received within the tubular extension and is tightly embraced therein to further promote a fluid-tight fit of said removable cap with said side port.

14. The improved hypothermic syringe of claim 12 wherein said barrel terminates in a collar surrounding said neck and radially spaced therefrom, said needle cover being releasably received on said collar in a substantially fluid-tight fit.

15. In a hypothermic syringe comprising
a barrel with an interior barrel sidewall defining an interior chamber, said barrel further having a narrowed opening at a forward end and a plunger opening at a rearward end,
an elongated plunger slidably received in the interior chamber in a fluid-tight embrace with the interior barrel sidewall,
a port in the barrel for accessing the interior chamber for withdrawing a specimen sample contained therein, said port being located proximate the narrowed opening and comprising an extension being canted at an angle relative to and extending from said barrel,
a removable cap engaging said port in a fluid-tight fit,
means for supporting the syringe in a skewered position with respect to horizontal located at a point proximate the rearward end of said barrel, such that when the syringe is placed on a horizontal surface with said supporting means in contact with the horizontal surface the syringe is inclined with the rearward end elevated relative to the forward end with the extension of said accessing means being substantially perpendicular to the horizontal surface, and
detachable means carried by said barrel and in contact with said plunger for one-way movement of said plunger for permitting said plunger to be moved away from the narrowed opening to admit material into said chamber, and preventing movement of said plunger toward the narrowed opening to express material from said chamber.

16. The hypodermic syringe of claim 15 wherein said plunger has an elongated body portion having a longitudinally extending rib, said rib having a series of notches spaced along its length, and wherein the means for one-way movement of said plunger comprises a resilient member carried on said barrel adjacent the plunger opening, the member having a portion angled radially inwardly relative to the axis of said barrel and extending in the direction of withdrawal of the plunger from the barrel chamber, the member being biased to engage the notches of the rib as the plunger is withdrawn from the chamber by alternatingly riding along a portion of the rib and then engaging a notch, whereby the angularity of the resilient member permits such seriatim withdrawing movement of the plunger and prevents reinserting movement of said plunger.

17. The hypodermic syringe of claim 15 wherein the plunger has an elongated body portion having a pair of longitudinally extending and opposed ribs, the ribs having a series of notches spaced along their lengths, and wherein the means for one-way movement of plunger comprises a member carried by the barrel adjacent the plunger opening having a pair of opposed resilient fingers, the fingers being angled radially inwardly relative to the axis of the barrel and extending in the direction of withdrawal of the plunger from the barrel, each finger further having a notch within which a respective notched rib is received, the fingers being biased to engage the notches of the ribs within the notches of the fingers, whereby the resilient member permits withdrawing movement of the plunger and prevents reinserting movement of the plunger.

18. The hypodermic syringe of claim 15 wherein said supporting means is a boss spaced inwardly along the barrel from the rearward end, the boss having generally a flat bottom.

19. The hypodermic syringe of claim 15 wherein said supporting means is a flange extending from said barrel immediately adjacent the plunger opening, said flange having a generally flat bottom on a side of said barrel opposite that of said port and also being adapted for manipulating said plunger.

20. An improvement in a hypodermic syringe having a barrel with an interior chamber and an exterior surface, a plunger opening in the barrel, and a plunger having an elongated body portion slidably received within the chamber, comprising a series of spaced detents extending longitudinally along the elongated body portion, and a detachable resilient member carried on the exterior surface of the barrel adjacent the plunger opening, the member having a portion angled radially inwardly relative to the axis of the barrel and extending in the direction of withdrawal of the plunger from the barrel, the member being biased to engage the detents of the body portion of the plunger seriatim as the plunger is withdrawn from the chamber by alternatingly riding along the body portion and then engaging a detent, whereby the resilent member permits withdrawing movement of the plunger and prevents reinserting movement.

21. The improved hypodermic syringe of claim 20 wherein the elongated body portion has a pair of opposed longitudinally extending ribs, each rib having a series of notches spaced along its length, and wherein the means for one-way movement of the plunger comprises a member carried by the barrel adjacent the plunger opening having a pair of opposed resilient fingers, the fingers being angled radially inwardly relative to the barrel and extending in the direction of withdrawal of the plunger from the barrel, each finger further having a notch within which a respective notched rib is received, the fingers being biased to engage the notches of the ribs within the notches of the fingers, whereby the resilient member permits withdrawing movement of the plunger and prevents reinserting movement of the plunger.

22. A hypodermic syringe for obtaining and transporting a fluid specimen comprising a barrel having a forward end and a rearward end and a narrowed opening at the forward end extending into a neck, a plunger slidably received through an opening at the rearward end into an interior chamber defined within said barrel, said plunger having resilient sealing means thereon engaging the interior barrel sidewall, such that the plunger is slidably received in the barrel and tightly embraced therein in a fluid-tight fit, an annular shaped extension of said barrel surrounding the neck and radially spaced therefrom, a protective cover detachably received on said annular extension in a substantially fluid-tight fit, said protective cover having an interior recess sufficiently long to receive a needle mounted on the neck, said protective cover adapted to protect a needle, and means for accessing the interior chamber of said barrel located at a point proximate the narrowed opening, said means comprising a tubular extension of small vertical height extending generally radially from said barrel.

23. The hypothermic syringe of claim 22 wherein said protective cover is a rigid elongated fluid-tight cap adapted to surround a needle.

24. The hypothermic syringe of claim 23 wherein the annular shaped extension surrounding the neck of said barrel and being radially spaced therefrom is provided with coarse screw threads for receiving corresponding screw threads of said protective cover to form a fluid-tight engagement.

25. The hypothermic syringe of claim 22 further comprising a hypothermic needle received on the neck of the narrowed opening.

26. A hypothermic syringe for obtaining a fluid specimen comprising a barrel having a forward end and a rearward end, an interior chamber defined by an interior barrel sidewall, a narrowed opening at the forward end extending into a neck, a plunger opening at the rearward end, and a flange extending radially from the barrel adjacent the plunger opening for manipulating a plunger, a plunger inserted in the chamber having resilient seal means thereon engaging the interior barrel sidewall, such that the plunger is slidably received in the barrel and tightly embraced therein in a fluid-tight fit, a hypothermic needle received on the neck of the narrowed opening, a port in the barrel proximate the narrowed opening and communicating with the interior of the chamber through which sampling instruments can be introduced into the interior of the chamber, said port has a tubular extension of small vertical height extending from the barrel defining a small hollow shaft into the chamber interior, and the closure has a protuberance slidably received in said shaft and tightly embraced therein when the closure is placed on the port, a substantially fluid-tight closure for the port, and a boss spaced inwardly along the barrel near the flange, the boss having a generally flat bottom such that the syringe when placed on a horizontal surface with the boss in contact with the surface will be inclined with the plunger opening raised relative to the narrow opening promoting pooling of specimen fluids near the narrowed opening and port.

27. In a hypothermic syringe for obtaining and transporting specimens for testing, the syringe including a barrel having a forward end and a rearward end, an interior chamber defined within the barrel, a narrowed opening at the forward end surrounded by a neck, a plunger opening at the rearward end, a plunger slidably received in the chamber and embraced therein in a fluid-tight engagement, a hypothermic needle received on the neck, and a flange extending from the barrel adjacent the plunger opening for manipulating the plunger, the improvement comprising a side port in the barrel for accessing the interior chamber with a sampling implement, the port being located immediately adjacent the narrowed opening, and a removable cap engaging the port in a fluid-tight fit, said port has a tubular extension of small vertical height extending generally radially from the barrel, a portion of the tubular extension being screw threaded, said port cap being match threaded for a screw fit with said port, said port cap further including a protuberance which is received within the tubular extension and is tightly embraced therein to further promote a fluid-tight fit of said port cap with said port.

28. In a hypothermic syringe including a barrel with an interior barrel sidewall defining an interior chamber, a narrowed opening at a forward end and a plunger opening at a rearward end and an elongated plunger slidably received in the chamber in a fluid-tight embrace with the interior barrel sidewall comprising, a port in the barrel for accessing the interior of the chamber for withdrawing a specimen sample contained therein, the port being located proximate the narrowed opening, a removable cap engaging the port in a fluid-tight fit, and means carried by the barrel and in contact with the plunger for one-way movement of the plunger, permitting the plunger to be moved away from the narrowed opening to admit material into the chamber, and preventing movement of the plunger toward the narrowed opening to express material from the chamber, the plunger has an elongated body portion having a longitudinally extending rib, the rib having a series of notches spaced along its length, and wherein said means for one-way movement of the plunger comprises a resilient member carried on the barrel adjacent the plunger opening, the member having a portion angled radially inwardly relative to the axis of the barrel and extending in the direction of withdrawal of the plunger from the barrel chamber, the member being biased to engage the notches of the rib as the plunger is withdrawn from the chamber by alternatingly riding along a portion of the rib and then engaging a notch, whereby the angularity of the resilient member permits such seriatim withdrawing movement of the plunger and prevents reinserting movement of the plunger.

29. The hypothermic syringe of claim 28 wherein the plunger has an elongated body portion having a pair of longitudinally extending and opposed ribs, the ribs having a series of notches spaced along their lengths, and wherein said means for one-way movement of plunger comprises a member carried by the barrel adjacent the plunger opening having a pair of opposed resilient fingers, the fingers being angled radially inwardly relative to the axis of the barrel and extending in the direction of withdrawal of the plunger from the barrel, each finger further having a notch within which a respective notched rib is received, the fingers being biased to engage the notches of the ribs within the notches of the fingers, whereby the resilient member permits withdrawing movement of the plunger and prevents reinserting movement of the plunger.

30. In a hypothermic syringe for obtaining and transporting a specimen for testing, the syringe comprising a barrel having a forward end and rearward end and interior chamber defined within said barrel, said barrel further having a narrowed opening at the forward end extending into a neck and a plunger opening at the rearward end, a plunger sized to pass through the plunger opening into the interior chamber and embrace therein in a fluid-tight engagement, a hypothermic needle received on the neck, a side port in said barrel for accessing the interior chamber with a sampling implement, said side port being located adjacent the narrowed opening, a removable cap engaging said side port in a fluid-tight fit, said side port has a tubular extension of small vertical height extending generally radially from said barrel, a portion of the tubular extension being screw threaded, said removable cap being match threaded for a screw fit with said side port, said removable cap further including a protuberance which is received within the tubular extension and is tightly embraced therein to further promote a fluid-tight fit of said removable cap with said side port, a flange extending from said barrel adjacent the plunger opening for manipulating said plunger, a protective cover for the needle, said protective cover being removably received on the barrel of the syringe and spaced radially from the neck, said protective cover when in use surrounds said needle and is spaced therefrom to protect said needle during transport, and an elongated boss carried by said barrel for supporting the syringe in an upright position and at an inclined angle on a horizontal surface, said boss being located near said flange and spaced therefrom inwardly along said barrel, said boss having a dimension substantially tangential to said barrel, and a small vertical height, such that when the syringe is placed on a horizontal surface with said boss in contact therewith, the syringe is inclined with the plunger opening elevated relative to said hypothermic needle to thereby pool specimen material in the chamber and near said port, the tubular extension of said port further being canted at an angle relative to said barrel such that the tubular extension is substantially vertical when the syringe is so placed on a horizontal surface.

31. In a hypothermic syringe for obtaining and transporting specimens for testing, the syringe including a barrel having a forward end and a rearward end, an interior chamber defined within the barrel, a narrowed opening at the forward end surrounded by a neck, a plunger opening at the rearward end, a plunger slidably received in the chamber and embraced therein in a fluid-tight engagement, a hypothermic needle received on the neck, and a flange extending from the barrel adjacent the plunger opening for manipulating the plunger, the improvement comprising a side port in the barrel for accessing the interior chamber with a sampling implement, said port being located immediately adjacent the narrowed opening, and a removable cap engaging said port in a fluid-tight fit, said port has a tubular extension of small vertical height extending generally radially from the barrel, a portion of the tubular extension being screw threaded, the port cap being match threaded for a screw fit with said port, the port cap further including a protuberance which is received within the tubular extension and is tightly embraced therein to further promote a fluid-tight fit of said port cap with the port, and an elongated boss carried by the barrel for supporting the syringe in an upright position and at an inclined angle on a horizontal surface, said boss being located near the flange and spaced therefrom inwardly along the barrel, said boss having a dimension substantially tangential to the barrel, and a small vertical height, such that when the syringe is placed on a horizontal surface with said boss in contact therewith, the syringe is inclined with the plunger opening elevated relative to the hypothermic needle to thereby pool specimen material in the chamber and near said port, the tubular extension of said port further being canted at an angle relative to the barrel such that the tubular extension is substantially vertical when the syringe is so placed on a horizontal surface.

* * * * *

UNITED STATES PATENT AND TRADEMARK OFFICE
CERTIFICATE OF CORRECTION

PATENT NO. : 4,958,622
DATED : September 25, 1990
INVENTOR(S) : William M. Selenke It is certified that error appears in the above-identified patent and that said Letters Patent is hereby corrected as shown below:

In claim 6, column 8, line 21, delete "immediate" and insert --immediately--.

In claim 7, column 8, line 42, delete "hypothermic" and insert --hypodermic--.

In claim 12, column 9, line 19, delete "hypothermic" and insert --hypodermic--.

In claim 12, column 9, line 29, delete "hypothermic" and insert --hypodermic--.

In claim 13, column 9, line 43, delete "hypothermic" and insert --hypodermic--.

In claim 14, column 9, line 53, delete "hypothermic" and insert --hypodermic--.

In claim 15, column 9, line 58, delete "hypothermic" and insert --hypodermic--.

In claim 16, column 10, lines 27, 28, 30, 31, 32, 33, 34, 35 and 36, change "the" to --said--.

UNITED STATES PATENT AND TRADEMARK OFFICE
CERTIFICATE OF CORRECTION

PATENT NO. : 4,958,622
DATED : September 25, 1990
INVENTOR(S) : William M. Selenke It is certified that error appears in the above-identified patent and that said Letters Patent is hereby corrected as shown below:

In claim 19, column 10, line 62, "port" should be --accessing means--.

In claim 23, column 11, line 57, delete "hypothermic" and insert --hypodermic--.

In claim 24, column 11, line 60, delete "hypothermic" and insert --hypodermic--.

In claim 25, column 11, lines 66 and 67, delete "hypothermic" and insert --hypodermic--.

In claim 26, column 12, lines 1 and 15, delete "hypothermic" and insert --hypodermic--.

In claim 27, column 12, lines 35 and 42, delete "hypothermic" and insert --hypodermic--.

In claim 28, column 12, line 59, delete "hypothermic" and insert --hypodermic--.

In claim 29, column 13, line 27, delete "hypothermic" and inser --hypodermic--.

UNITED STATES PATENT AND TRADEMARK OFFICE
CERTIFICATE OF CORRECTION

PATENT NO. : 4,958,622

DATED : September 25, 1990

INVENTOR(S) : William M. Selenke

It is certified that error appears in the above-identified patent and that said Letters Patent is hereby corrected as shown below:

In claim 30, column 13, lines 44 and 54, delete "hypothermic" and insert --hypodermic--.

In claim 30, column 14, line 21, delete "hypothermic" and insert --hypodermic--.

In claim 31, column 14, lines 27, 34, 60 and 61, delete "hypothermic" and insert --hypodermic--.

Signed and Sealed this

Seventh Day of April, 1992

Attest:

HARRY F. MANBECK, JR.

*Attesting Officer*   Commissioner of Patents and Trademarks